(12) United States Patent
Crocker

(10) Patent No.: US 6,890,319 B1
(45) Date of Patent: May 10, 2005

(54) APPARATUS FOR DELIVERING A SUBSTANCE HAVING ONE OR MORE NEEDLES DRIVEN AT HIGH VELOCITY

(75) Inventor: Peter John Crocker, Surrey (GB)

(73) Assignee: Imprint Pharmaceuticals Ltd., Surrey (GB)

( * ) Notice: Subject to any disclaimer, the term of this patent is extended or adjusted under 35 U.S.C. 154(b) by 0 days.

(21) Appl. No.: 09/762,887

(22) PCT Filed: Aug. 13, 1999

(86) PCT No.: PCT/GB99/02680

§ 371 (c)(1),
(2), (4) Date: Feb. 12, 2001

(87) PCT Pub. No.: WO00/09184

PCT Pub. Date: Feb. 24, 2000

(30) Foreign Application Priority Data

Aug. 13, 1998 (GB) .............................................. 9817662

(51) Int. Cl.⁷ ................................................ A61M 5/20
(52) U.S. Cl. ...................................... 604/131; 604/156
(58) Field of Search .................................. 604/156, 131

(56) References Cited

U.S. PATENT DOCUMENTS

| | | | |
|---|---|---|---|
| 2,634,726 A | 4/1953 | Hanson | 128/221 |
| 2,862,495 A | 12/1958 | Gewecke | 128/221 |
| 3,181,336 A | 5/1965 | Schofield | 72/340 |
| 3,788,315 A | 1/1974 | Laurens | 128/173 |
| 3,840,008 A | 10/1974 | Noiles | 128/221 |
| 3,957,051 A | 5/1976 | Topham | 128/278 |
| 3,964,482 A | 6/1976 | Gerstel et al. | 128/260 |
| 4,031,892 A | 6/1977 | Hurschman | 128/218 |
| 4,188,949 A | 2/1980 | Antoshkiw | 128/218 |
| 4,193,400 A | 3/1980 | Loveless et al. | 128/214.4 |
| 4,203,446 A | 5/1980 | Hofert et al. | 128/329 |
| 4,204,438 A | 5/1980 | Binaris et al. | 81/9.22 |
| 4,214,490 A | 7/1980 | Chizek | 81/9.22 |
| 4,257,561 A | 3/1981 | McKinney | 239/581 |
| 4,286,599 A | 9/1981 | Hahn et al. | 128/316 |
| 4,351,335 A | 9/1982 | Whitney et al. | 128/218 |
| 4,383,530 A | 5/1983 | Bruno | 604/274 |
| 4,392,493 A | 7/1983 | Niemeijer | 128/316 |
| 4,411,657 A | 10/1983 | Galindo | 604/274 |
| 4,413,993 A | 11/1983 | Guttman | 604/274 |
| 4,437,361 A | 3/1984 | Steckel et al. | 81/9.22 |
| 4,447,232 A | 5/1984 | Sealfon et al. | 604/134 |
| 4,508,106 A | 4/1985 | Angres | 128/1 |
| 4,535,769 A | 8/1985 | Burns | 128/314 |
| 4,537,593 A | 8/1985 | Alchas | 604/411 |
| 4,582,060 A | 4/1986 | Bailey | 128/316 |
| 4,592,744 A | 6/1986 | Jagger et al. | 604/192 |
| 4,613,328 A | * 9/1986 | Boyd | 604/156 |
| 4,634,431 A | 1/1987 | Whitney et al. | 604/155 |
| 4,665,912 A | 5/1987 | Burton | 128/303 |
| 4,666,438 A | 5/1987 | Raulerson | 604/272 |
| 4,671,277 A | 6/1987 | Beuchat | 128/316 |
| 4,699,692 A | 10/1987 | Autio | 162/199 |

(Continued)

FOREIGN PATENT DOCUMENTS

| | | | |
|---|---|---|---|
| DE | 3405671 | 8/1985 | |
| EP | 058.536 | 4/1986 | .......... A61M/5/315 |
| WO | 9220388 | 11/1992 | |
| WO | WO92/20388 | 11/1992 | ............ A61M/5/20 |

*Primary Examiner*—Philippe Derakshani
(74) *Attorney, Agent, or Firm*—Ronald B. Sherer; Bartlett & Sherer

(57) ABSTRACT

An apparatus for delivering a substance to a surface, such as the skin of a human being, animal or other organic matter has a needle. Also provided is means for supplying the substance to the tip of the needle in use, and driving means for driving the needle, in use, at a velocity in the range of 1 meter per second to 100 meters per second in order to penetrate the surface and deliver the substance thereto.

68 Claims, 9 Drawing Sheets

U.S. PATENT DOCUMENTS

| | | | | |
|---|---|---|---|---|
| 4,710,180 | A | 12/1987 | Johnson | 604/239 |
| 4,719,825 | A | 1/1988 | LaHaye et al. | 81/9.22 |
| 4,771,660 | A | 9/1988 | Yacowitz | 81/9.22 |
| 4,781,689 | A | 11/1988 | Sealfon et al. | 604/134 |
| 4,790,830 | A | 12/1988 | Hamacher | 604/274 |
| 4,808,170 | A | 2/1989 | Thornton et al. | 604/274 |
| 4,838,877 | A | 6/1989 | Massau | 604/272 |
| 4,842,587 | A | 6/1989 | Poncy | 604/198 |
| 4,862,772 | A | 9/1989 | Piperato | 81/9.22 |
| 4,889,529 | A | 12/1989 | Haindl | 604/274 |
| 4,895,147 | A | 1/1990 | Bodicky et al. | 606/182 |
| 4,914,988 | A | 4/1990 | Chang | 81/9.22 |
| 4,921,475 | A | 5/1990 | Sibalis | 604/20 |
| 4,924,879 | A | 5/1990 | O'Brien | 128/770 |
| 4,931,059 | A | 6/1990 | Markham | 606/185 |
| 4,968,302 | A | 11/1990 | Schluter et al. | 604/135 |
| 4,990,135 | A | 2/1991 | Truesdale, Jr. | 604/47 |
| 5,054,339 | A | 10/1991 | Yacowitz | 81/9.22 |
| 5,060,658 | A | 10/1991 | Dejter, Jr. et al. | 128/753 |
| 5,061,250 | A | 10/1991 | Shields | 604/198 |
| 5,076,282 | A | 12/1991 | Fishman et al. | 128/743 |
| 5,225,750 | A | 7/1993 | Higuchi et al. | 318/280 |
| 5,244,120 | A | 9/1993 | O'Meara | 222/94 |
| 5,250,067 | A | 10/1993 | Gelfer et al. | 606/189 |
| 5,262,128 | A | 11/1993 | Leighton et al. | 422/100 |
| 5,271,744 | A | 12/1993 | Kramer et al. | 604/51 |
| 5,279,552 | A | 1/1994 | Magnet | 604/47 |
| 5,318,584 | A | 6/1994 | Lange et al. | 606/182 |
| 5,364,374 | A | 11/1994 | Morrison et al. | 604/272 |
| 5,401,242 | A | 3/1995 | Yacowitz | 604/48 |
| 5,443,492 | A | 8/1995 | Stokes et al. | 607/131 |
| 5,451,210 | A | 9/1995 | Kramer et al. | 604/137 |
| 5,454,922 | A | 10/1995 | Joshi et al. | 204/265 |
| 5,472,449 | A | 12/1995 | Chou | 606/186 |
| 5,496,304 | A | 3/1996 | Chasan | 606/1 |
| 5,515,871 | A | 5/1996 | Bittner et al. | 128/898 |
| 5,564,436 | A | 10/1996 | Hakky et al. | 128/754 |
| 5,580,859 | A | 12/1996 | Felgner et al. | 514/44 |
| 5,611,806 | A | 3/1997 | Jang | 606/167 |
| 5,681,283 | A | 10/1997 | Brownfield | 604/136 |
| 5,697,901 | A | 12/1997 | Eriksson | 604/46 |
| 5,716,348 | A | 2/1998 | Marinacci et al. | 604/272 |
| 5,752,942 | A | 5/1998 | Doyle et al. | 604/274 |
| 5,807,275 | A | 9/1998 | Jamshidi | 600/567 |
| 5,848,991 | A | 12/1998 | Gross et al. | 604/140 |
| 5,848,996 | A | 12/1998 | Eldor | 604/272 |
| 5,860,957 | A | 1/1999 | Jacobsen et al. | 604/156 |
| 5,868,721 | A | 2/1999 | Marinacci et al. | 604/272 |
| 5,911,703 | A | 6/1999 | Slate et al. | 604/68 |
| 6,030,404 | A | 2/2000 | Lawson et al. | 606/186 |
| 6,057,090 | A | 5/2000 | Mikoshiba et al. | 430/607 |
| 6,065,371 | A | 5/2000 | Yacowitz | 81/9.22 |
| 6,068,855 | A | 5/2000 | Leslie et al. | 424/468 |
| 6,077,247 | A * | 6/2000 | Marshall et al. | 604/156 |
| 6,270,479 | B1 * | 8/2001 | Bergens et al. | 604/156 |

* cited by examiner

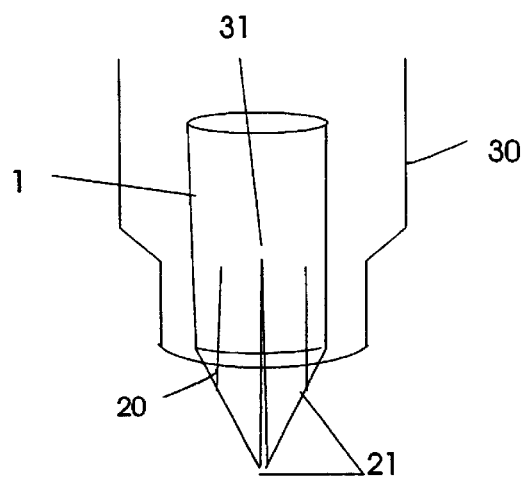
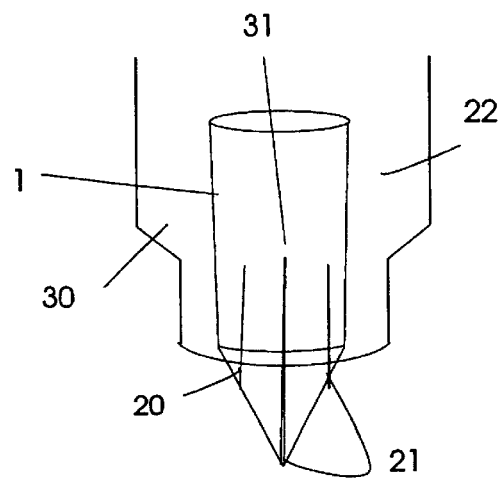
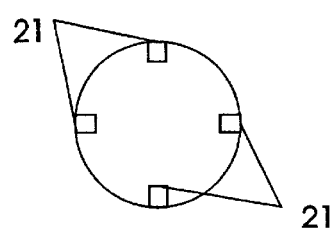
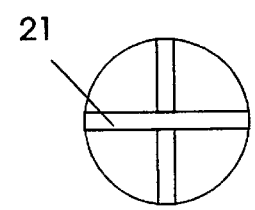
Fig. 3A　　　　　　　　　Fig. 3B

APPARATUS FOR DELIVERING A SUBSTANCE HAVING ONE OR MORE NEEDLES DRIVEN AT HIGH VELOCITY

This invention relates to improvements in devices for delivery of substances such as drugs, vaccines, fluorescent or magnetic material, and dyes into a surface, such as the skin of a human being, animal or other organic matter. The substance may be a solution, particulate fluid, or a paste, for example.

Numerous such apparatus have been proposed in the past. A simple hypodermic syringe is the most well known, although other mechanical arrangements, such as a standard tattooing machine which are manually operated are well known.

In order to improve the injection of substances mechanically driven needles are also in use. U.S. Pat. Nos. 5,401,242, 5,054,339, 4,671,277 disclose mechanically operated systems which inject substances such as drugs, vaccines, pigment etc. into the skin. A problem with this type of system is that their use can cause considerable pain to the person or animal to which they are being applied and can, in extreme circumstances, such as that of a standard tattooing machine, damage the skin to such an extent that recovery takes several days. This last point has prevented tattooing machines being used for drug delivery U.S. Pat. No. 5,681,283 discloses the use of a system in which needles are injected into the skin using elastic bands at a higher velocity with the intention of making the injection "painless".

U.S. Pat. No. 5,564,436 discloses a pneumatically operated automatic rotating cassette with a plurality of stylets so that the higher velocity can reduce the pain of the of needle entry.

Many of these devices have disadvantages in that they are unable to dispense accurate amounts of a substance, particularly when small volumes or multiple doses are required, and in that they are unable to deliver the substance reliably to a desired depth.

Also these devices are often difficult for an unskilled operator to use, and are not viable for self administration applications. Furthermore, these apparatus are often unable to deliver substances without reliably ensuring that no substance is left on the surface of the skin, meaning that they often cannot be employed to deliver valuable or potentially toxic substances.

Also these devices use needle acceleration and velocity which is insufficient to obtain needle entry which is pain and blood free.

Also these devices are prone to permit significant levels of lateral or transaxial movement of the needle during penetration of the skin casing extra damage and trauma. This becomes more significant as the acceleration and velocity increases.

Also these devices require needles which have cutting edges and are substantially cutting rather than parting in action causing tissue damage, bleeding, bruising etc.

The present invention is directed towards overcoming the above and other problems.

According to the present invention there is provided an apparatus for delivering a substance to a surface, such as the skin of a human being, animal or other organic matter, the apparatus comprising:
  a needle;
  means for supplying the substance to the tip of the needle in use;
  and means for driving the needle, in use, at a velocity in the range of 1 meter per second to 100 meters per second at the time when the needle first contacts the skin in order to penetrate the skin and deliver the substance thereto.

Preferably the driving means drives the needle at a velocity of at 5 to 50 meters per sec, more preferably 6 to 35 meters per sec. at the time when the needle first contacts the skin.

By driving the needle at very high velocity, as opposed to a normal tattooing machine which operates at approximately 0.6 meters per second, an auto-injector or a lancet which operates at 0.5 to 4 meters per sec., it has been determined that the amount of pain experienced by the recipient of the substance is reduced considerably. Although high speed has been stated to reduce the pain of injection the very high speeds of the present invention have not previously been disclosed.

The use of ultra high speeds e.g. in excess of 100 meters per second has been found to cause bruising and increase in pain and it is very surprising that the use of velocities in the range specified in the invention gives an improved reduction in pain. In addition the use of ultra high velocities requires greater energy and increases safety problems and generates a lot of noise which can be disconcerting to a user, particularly in self administration, and also imposes a great deal of wear on the equipment with consequent increase risk of failure.

It is preferred that when the needle enters the surface it is moving at or near its maximum velocity and it is brought to a very rapid stop e.g. by there being a stopping means incorporated in the driving means and this also aids in controlling the depth of penetration. This use of a stopping means to bring the needle to a sudden stop enables more effective injection and enables the substance being injected to be injected at a shallow depth in the skin when required. The sudden stop also has the advantage that the momentum of the substance being injected can be used to facilitate the injection of the substance.

The needle driving means may include one or more of a leaf spring and stop arrangement, a bistable spring or diaphragm arrangement. The needle driving means may include a mechanically hydraulic, pneumatic or electromechanically driven drive mechanism.

There are different types of injections, for example the needle can be driven through the skin to inject a substance into the subcutaneous layer e.g. to a depth of 10 to 12 mm, such as in injections of vaccines, insulin, etc. or the needle can be driven deeper to penetrate muscle for intramuscular injection, or the needle can be driven only a small distance into the skin, and the apparatus of the present invention can be used for these and a wide range of other types of injections.

For use in some injections there is preferably a means whereby a series of injections take place sequentially and rapidly one after the other with preferably only a small amount of the substance injected with each penetration of the needle, in this way the total amount of substance to be injected is injected in a series of small amounts with less risk of bruising etc. due to deeper penetration of the needle. The rate of injection of the needle can be up to 50 times a second or higher and the driving means mechanism incorporates a means to drive the needle repeatedly a small distance into the skin.

The diameter of the needles may be in the range of 10 to 1000 microns or more, and may be arranged so that they form 1 to 5000 holes per square centimeter. With such a needle arrangement the needles may be designed to penetrate to a depth of 10 microns upwards e.g. 30 microns and upwards, dependent upon the substance being delivered and the surface to which the substance is being applied. The needle may contain one or more edges but, preferably is substantially non-cutting with smooth tapered, beveled or radiused surfaces for example a pencil tip point.

When a rapid series of injections which penetrate a small distance into the skin are required the driving means can be motorised to generate a rapid succession of small injections.

When an injection which penetrates a controlled depth into the surface is required a preferred driving means is pneumatically operated and comprises a block slidably mounted in a conduit so that application of a pneumatic force at one end of the conduit will generate a pulse of air which will propel the block at speed down the conduit, so that it will strike an end piece which forms part of, or is connected to the needle.

Preferably the block can be returned to its original position by reduction of pressure in the conduit. In this way a series of pulsed impulses can be applied to the end piece with the block being withdrawn back down the conduit between pulses.

The end piece which is struck can be the end of the needle suitably reinforced if need be, or it can be an end piece or the like attached to or forming part of the end of the needle. The end piece will normally have a flat end which is struck for ease of operation although this is not essential The pneumatic force can be applied by a means which generates a pulse of air down the conduit which sends the block down the conduit at the required velocity, reversal of the pressure will cause the block to be sucked back up the conduit. Suitable means include hand held bellows, a piston with a spring return or a motorised means. The bellows can, for example be in the form of a sealed rubber chamber connected to the conduit. Another means of operating is by means of a pen injector which can be conveniently carried and used as required.

If a rapid series of injections are required e.g. in which the needle penetrates only a small distance into the skin, a motorised means can be used to generate the pulse of air and subsequent reversal of pressure.

In another embodiment of the invention there is provided a means whereby the needle is driven into the skin in one or more steps by applying a blow to the needle e.g. as described above, so that the needle penetrates a controlled distance into the skin and optionally another blow or blows can be applied to the needle to drive the needle in further in if desired.

If a plurality of blows are required this can be carried out as described above and/or there can a two or more blocks slidably mounted within the conduit so that a plurality of blows impact on the plate.

Optionally there can be a needle guide which can fit around the needle to assist in the location and positioning of the needle and keeps the needle exactly on line during the injection and reduces any risk of the needle bending. In addition the guide can help guard against needle stick injury when the needle is withdrawn and can serve as a depth control.

In one embodiment of the invention the substance to be injected is contained in a reservoir fluidically connected to the needle and there are means to accelerate the needle independently without accelerating the reservoir. This means that there is less mass to be accelerated to the requisite velocity and so it is easier to attain this velocity and also to stop the needle. The acceleration of the needle is preferably 1 to 20,000 g.

The mass of the needle and associated moving parts is preferably 0.01 to 2.5 grm, more preferably 0.1 to 2 grms and most preferably 0.3 to 1 grm., this also means that the needle and other connected components have less kinetic energy and this reduces the risk of bruising etc. This is different to other techniques of injection, such as the injection of animals with tranquillising darts, when the needle penetrates the surface and forms part of, or is rigidly connected directly to a chamber containing the substance to be injected.

The needle can be separate and adjacent to a syringe containing the substance to be delivered with one end of the needle flexibly connected to the end of the syringe by for example a flexible tube or by a coiled length of the needle so that rapid movement of the needle is not significantly inhibited by connection to the syringe. The needle is driven by the driving means until it has penetrated to the required depth and then the syringe is operated to inject the substance contained in the syringe through the needle into the surface.

In another embodiment a syringe has a piston operating in the normal way with the needle projecting through the end of the syringe and having an extension projecting through the piston so the end of the extension can be struck by a driving means to drive the needle into a surface, there being a connection means between the syringe and the needle whereby the substance in the syringe can pass through the needle from the syringe as the piston is depressed. In use the needle is placed against the surface and the end of the extension is struck as referred to above to drive the needle into the surface and then, when it has been driven into the required depth, the piston is depressed to inject the substance in the syringe into the surface.

Preferably the needle is driven into the skin of the user by applying one or more impacts to the needle to drive the needle into the skin to the desired controlled depth and then the substance to be delivered is applied through the needle; the pneumatically driven method referred to above is especially suitable for this.

It has been found that, with the apparatus of the invention a needle used for at least some applications can be blunter i.e. it has a rounded or conical tip and has no, or less sharp, cutting surfaces than typical hypodermic or lancet needles and this structure can cause less cutting of capillaries and bleeding. This is thought to be due to the blunter needle, when driven at the speeds of the present invention, forces the components of the skin such as capillaries, cells etc. apart rather than cutting them as would be done with sharper needles. This reduces the risk and incidence of pain and bruising and the possible formation of unsightly fibroids and the like. For some people such as haemophiliacs this is a great advantage.

This advantage was surprising and contrary to what would otherwise be thought.

For persons who have to have frequent injections such as diabetics, who need to inject insulin on a regular basis, the reduction of bruising, bleeding etc. is also a great advantage and this embodiment is particularly applicable for use with such people.

After injection the needle can then be withdrawn from the surface and it has been found that, in at least some applications, a relatively slow withdrawal of the needle can reduce the risk of bruising to the skin.

For other applications, faster withdrawal of the needle is beneficial and can be achieved by a compressed spring for example.

It has been determined that with the present invention, the substance is delivered such that little residue is left on the surface of the skin.

A needle which can be used in the present invention has a sharpened tip and substance retaining core, the tip having at least one aperture formed therein, the at least one aperture connecting the core of the needle with the exterior of the tip of the needle and having a cross-sectional area smaller than the core, so that, in use, the needle can be driven into the skin in order to deliver the substance from the core to the skin without the aperture pulling out skin/tissue during its removal.

By providing a needle which does not have apertures of such shape, orientation or location which draws up skin upon removal of the needle damage to the skin by the apparatus is reduced significantly. Furthermore, blockage of the apertures and contamination of the substance supply by withdrawn skin particles is reduced significantly.

Plural apertures may be provided.

The one or more apertures may have a circular cross-section, or may, alternatively, have a slot or a cross shaped cross-section.

The needle may be hollow in order to provide the substance supplying core and preferably the needle has a hole in a recess so that the sides of the needle aperture do not press against the skin. Alternatively, the needle may be formed from a solid sharpened member. The needle is preferably slidably retained with a housing, the housing may define the core. With the latter arrangement, the one or more apertures may be provided within the sharpened member, between the sharpened member and the housing or a combination thereof. The grooves may define the core, in the case of a solid needle member.

If the needle is provided by a central sharpened member and surrounding housing, the housing may be arranged to surround the needle to prevent lateral movement thereof, hence reducing damage to the skin. The housing can also serve to prevent needle stick injury after use.

With such an arrangement, the housing may be angled to control the angle of entry of needle to a skin, or may be arranged so that the angle of entry can be controlled either manually or automatically.

The one or more needles may be retained on a flexible pad which is placed or attached adjacent to the skin prior to insertion of the needle; The flexible pad may include a substance reservoir in fluid communication with the one or more substance retaining cores or apertures in the skin. As the needle penetrates the reservoir in the pad it and then enters the skin it causes the substance in the pad to be injected into the skin.

The needle can be struck by the device described above causing rapid acceleration to penetrate the skin painlessly.

According to another aspect of the present invention there is also provided an apparatus for delivering a substance to the skin of a human being, animal or other organic matter, the apparatus comprising:

- a needle;
- a chamber surrounding the needle for retaining, in use, the substance to be delivered; and
- a membrane defining one wall of the chamber, the relative positions of the needle and membrane being such that, in use, the needle can be driven through the membrane and into and out of the skin to thereby deliver the substance.

The needle may be any one of the configurations described above. The membrane may be formed from an elastomer, such as silicone rubber.

The needle may be driven through the membrane by a high velocity driving mechanism of the type described above. Alternatively, it may be driven through the membrane by a user-generated force. The membrane may be arranged to be attached, in use, to the skin.

The provision of a chamber partly defined by a membrane ensures that the substances kept sterile and out of contact with the environment prior to use. Furthermore, the employment of a membrane prevents needle-stick injury both before and after needle deployment. In addition, it minimises spillage of the substance.

With any of the above arrangements means may be provided for detecting the depth of penetration of the skin by the needle, and the depth of penetration may be able to be controlled either by the user or automatically in response to detection of penetration depth. The penetration depth may be detected by applying a voltage potential to and measurement of the resulting current flowing through the skin between two needles, or the needle, skin and a detection point placed on the skin.

The invention is illustrated by example in the following non limiting examples.

EXAMPLE 1

Single Needle Penetration

A tube and pneumatic drive was used to accelerate a block at 0.4 g to a velocity of 5–15 meters per sec. To strike a radius tip 28 gauge needle assembly weighing 0.2 g adjacent to the skin. The needle contained a lateral hole adjacent to the tip and was driven 10 mm into the skin of the arm with no pain, was able to deliver a small quantity of sterile saline to the skin and left no blood or bruising on withdrawal.

For comparison an injection device was tested which fired a 29 gauge bevel tip hypodermic needle at 4 meters per sec. into the skin of the arm to a depth of 11 mm. There was significant pain, some bleeding after withdrawal of the needle and bruising developed around the penetration sight taking 5 days to disappear.

EXAMPLE 2

Multiple Shallow Micro Injections

A shuttle weighing 0.9 g comprising a needle with a tip aperture as described in Fig. below attached to a micro-syringe containing a dye was accelerated to 5 to 15 meters per sec. Towards the skin of the arm of a male volunteer. The needle penetrated to 0.3 mm before stopping rapidly at the end stop. The momentum of the fluid and piston in the micro-syringe created a short pressure pulse to deliver a small quantity of dye to the skin. The cycle was repeated a number of times in rapid succession. The injections were painless and did not bleed.

Further examples of the present invention will now be described with reference to the accompanying drawings, in which:

FIGS. 1A and 1B are schematic diagrams of a first example of the present invention;

FIGS. 2A to 2D are schematic side cross-sectional views of a second example of the present invention, FIGS. 3A and 3B are further schematic side cross-sectional views of the second example of the present invention;

FIGS. 4A and 4B are schematic side cross-sectional views of a third example of the present invention;

FIG. 5 is a schematic side cross-sectional view of a fourth example of the present invention;

FIGS. 6A and 6B are schematic side cross-sectional views of a fifth example of the present invention;

FIG. 7 is a view of sixth example of the invention

Figure 1A:
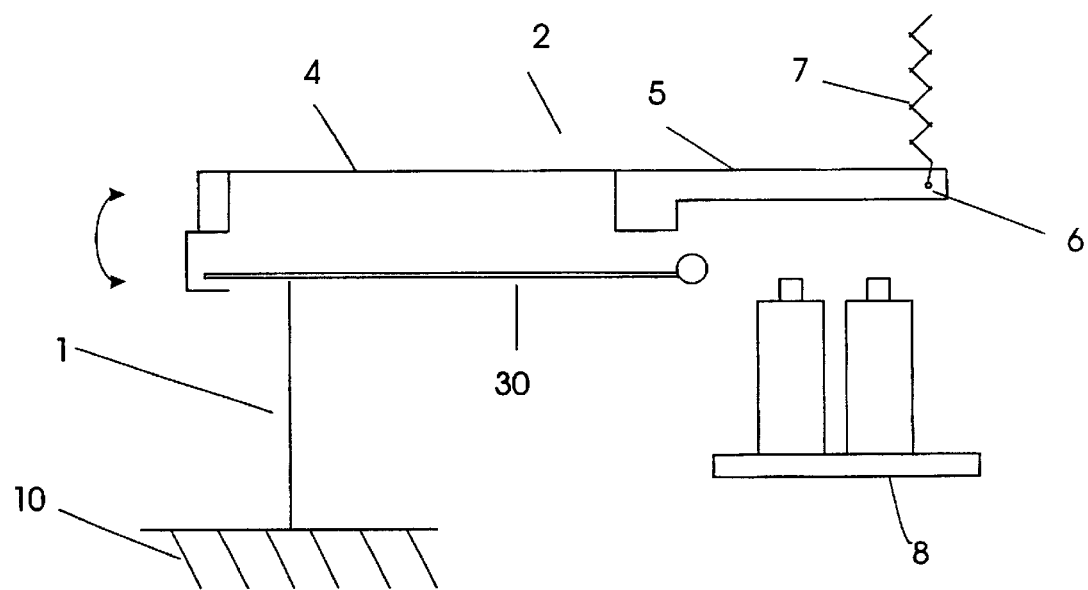

Referring to FIG. 1A, a first example of the present invention has a needle 1 attached to a drive mechanism 2. The drive mechanism 2 comprises a lever 3 and spring 4. The spring 4 is, in this example a leaf spring, although alternative spring arrangements may be provided. The spring 4 is attached to a magnetic drive member 5. The magnetic drive member 5 is moved about a pivot axis 6 by a combination of a spring 7 and solenoid 8. In use, the drive member 5 is driven into engagement with the lever 3 by the generation of a magnetic field by the solenoid 8. The magnetic field is then cut off and the drive member 5 is drawn out of engagement with the lever 3 by force generated in the spring 7. In such a manner the drive member 5 can be driven into and out of engagement with the lever 3 in a pulsed manner. The engagement of the drive member 5 with the lever 3 urges the tip line of the needle 1 into skin 10 to which a substance is to be applied.

The lever 3 acts to increase the velocity with which the needle moves given the driving velocity of the drive member 5.

The spring 4 is provided to increase yet further the velocity of the needle. In use, the needle 1 is driven in and out of the skin 10 at high velocity, a substance (not shown), which may either be liquid or particulate, is provided to the tip 9 of the needle 1 in a manner of the type described below or in another well known manner. Withdrawal of the needle generates a vacuum in the hole created by the needle's departure, and the substance is drawn into the generated hole. This arrangement has the advantage that no pump is required to supply substance to the needle tip.

Figure 9:
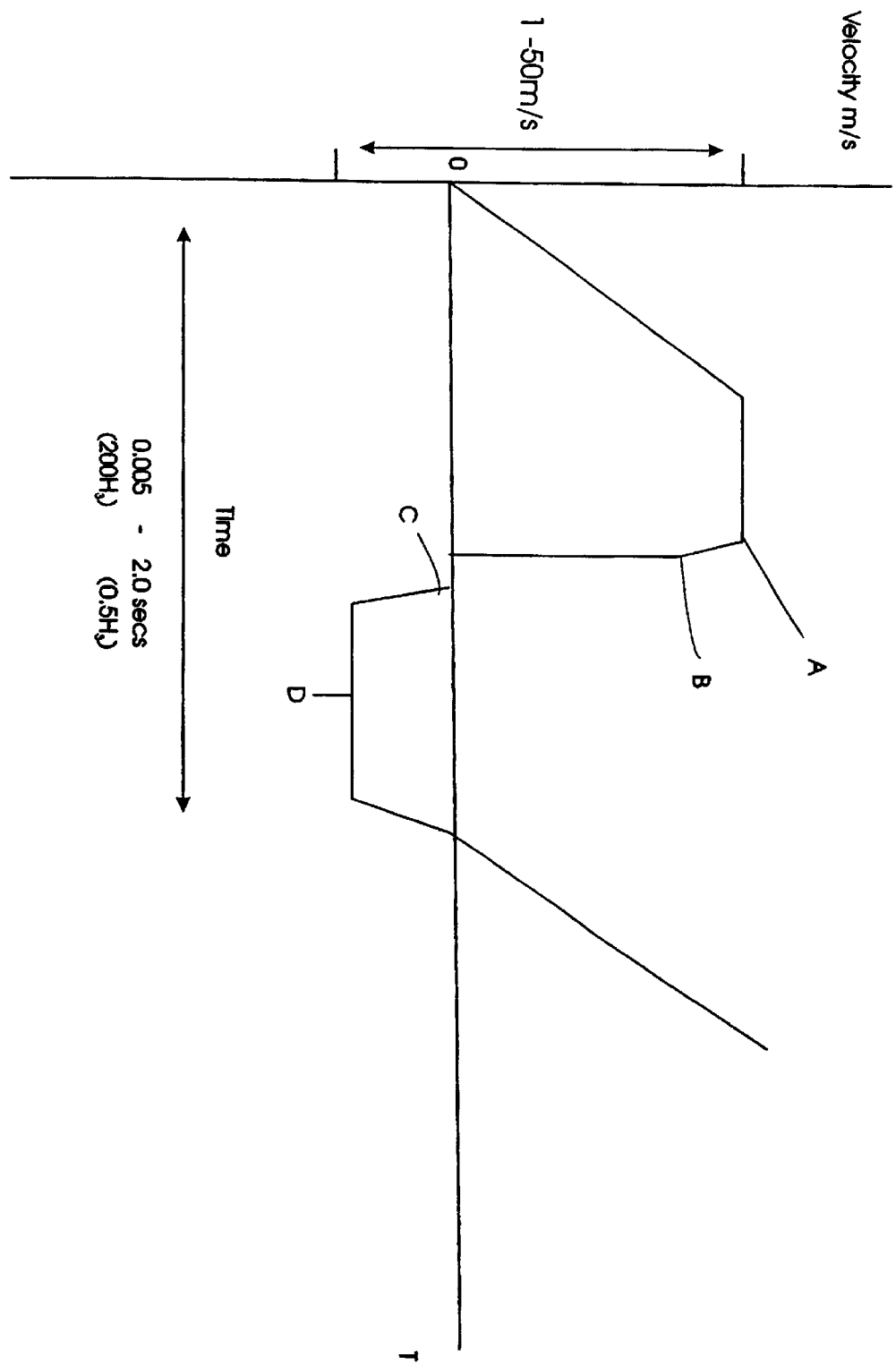
FIG. 9 is a graph showing the velocity versus time of a needle driven by an example of the present invention.

FIG. 9 shows an example velocity profile of an example of the present invention.

As can be seen from FIG. 9, the needle is initially accelerated to a high velocity for skin penetration. At point A the needle hits the skin, and at point B the needle hits an end stop, causing the needle 1 to decelerate rapidly. Upon withdrawal (point C) there is initial high acceleration to counter limiting friction with the skin and in order to ensure minimum damage to the skin, this is then followed by a phase D to ensure optimum substance delivery. It will be noted that the cycle is asymmetric, but this is not essential. In some embodiments where the substance is applied under external pressure e.g. from a syringe, the withdrawal acceleration should occur after the substance delivery phase D. in some embodiments the acceleration C is much lower acceleration.

Figure 1B:
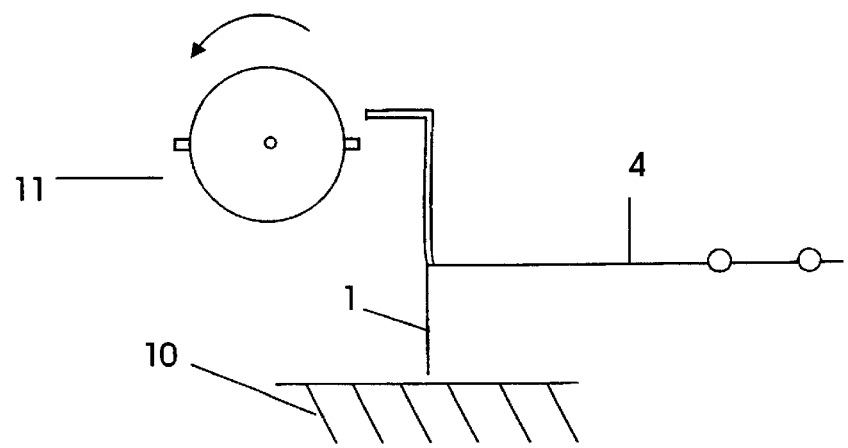

FIG. 1B is a schematic diagram, in which features corresponding to those in FIG. 1A are numbered identically. In this arrangement, a motor and cam arrangement 11 acts against a leaf spring 4 to generate a reciprocating motion in the needle 1.

With the arrangements of both FIGS. 1A and 1B the drive mechanism is arranged such that the needle is driven towards the skin 10 at a velocity of at least 1 meter per second and preferably much higher, so that the pain felt by a recipient of the substance is minimised. Also, the withdrawal is controlled to optimise substance delivery, as discussed above.

FIGS. 2A to 2D show needle arrangements which may be employed with the example of FIGS. 1A and 1B, or may be employed in more conventional needle driving apparatus.

Figure 2A:
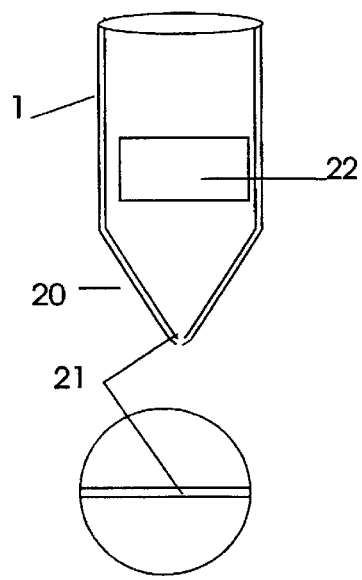
Figure 2B:
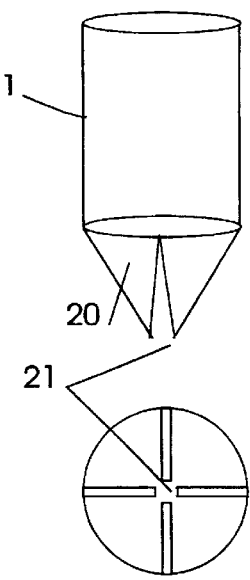
Figure 2C:
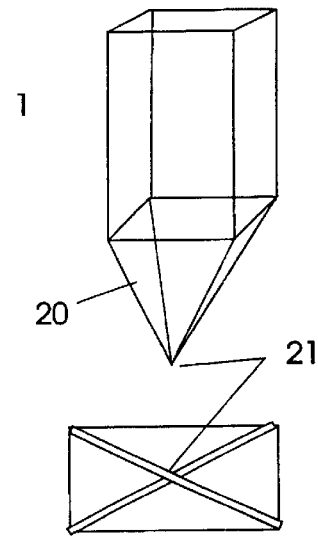

Referring to FIG. 2A, the needle 1 has a sharp tip 20 and is of hollow construction. Formed in the sharp tip 7 is an aperture 21, which in FIG. 2A is a slot, and which in FIG. 2B and FIG. 2C is a cruciform. The aperture 21 in each of the examples of FIGS. 2A to 2C passes from the core of the needle to the exterior. In use, the tip 20 of the needle 1 is driven into the skin and, during withdrawal of the needle 1, the partial vacuum created in the aperture formed by the tip 20 and needle 1 draws a substance 22 from the core of the needle 1 out into the skin. An important feature of all of the aperture 10 configurations shown in FIGS. 2A to 2D is that the shape, orientation, and cross-sectional area of the aperture or apertures 21 are small enough that they do not draw a core of skin through them upon entry of the needle 1 into the skin, and do not draw skin out upon removal, but allow flow 15 of substance 22 during withdrawal.

Figure 2D:
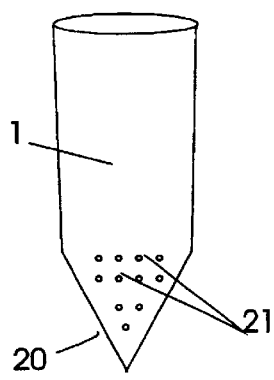
Figure 2D:
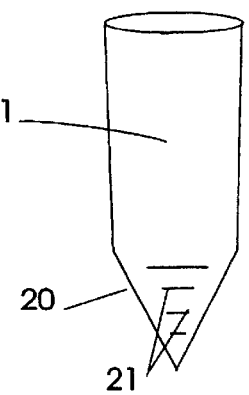
Figure 2D:
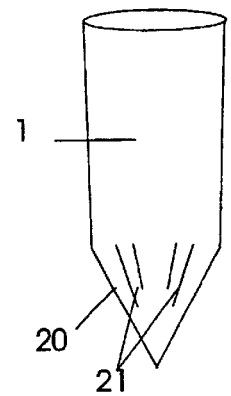

FIG. 2D shows the employment of plural apertures 21, which may be either circular or slot-like.

The needles shown in any of the figures may be formed by any well known forming, turning, laser machining, or moulding technique. The diameter of the needles may be in the range of 10 to 1000 microns, and may be arranged so that there are 1 to 5000 holes per square centimeter. With such a needle arrangement the needles may be designed to penetrate to a depth of 10 microns upwards e.g. 30 microns and upwards, dependent upon the substance being delivered and the surface to which the substance is being applied.

FIGS. 3A and 3B show alternative examples to the arrangement shown in FIGS. 2A to 2B. In these examples, the needle 1 comprises a housing 30 in which a substance 22 to be delivered is retained. Slidably retained within the housing 30 with a member 31 which has a sharpened tip 20. The member 31 is driven in the same manner as the previous example, and has an aperture or apertures 21 formed in it. This example operates in a manner similar to that of the examples in FIGS. 2A to 2D, in that the substance 22 is drawn into skin 10 via apertures 21 during withdrawal of the needle.

Figure 4A:
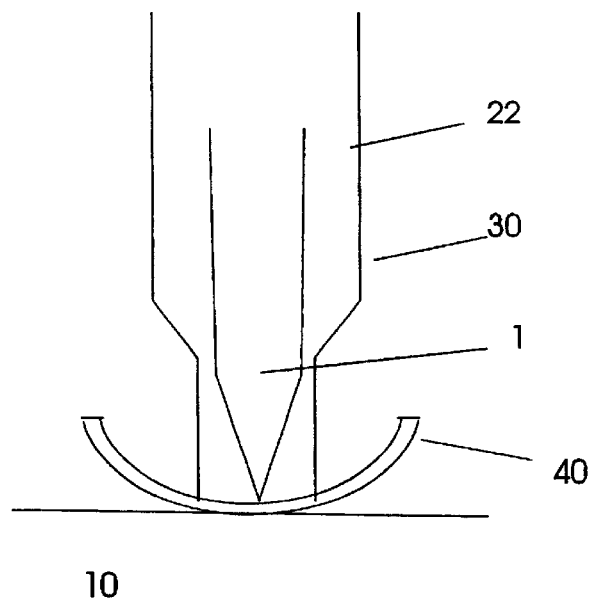
Figure 4B:
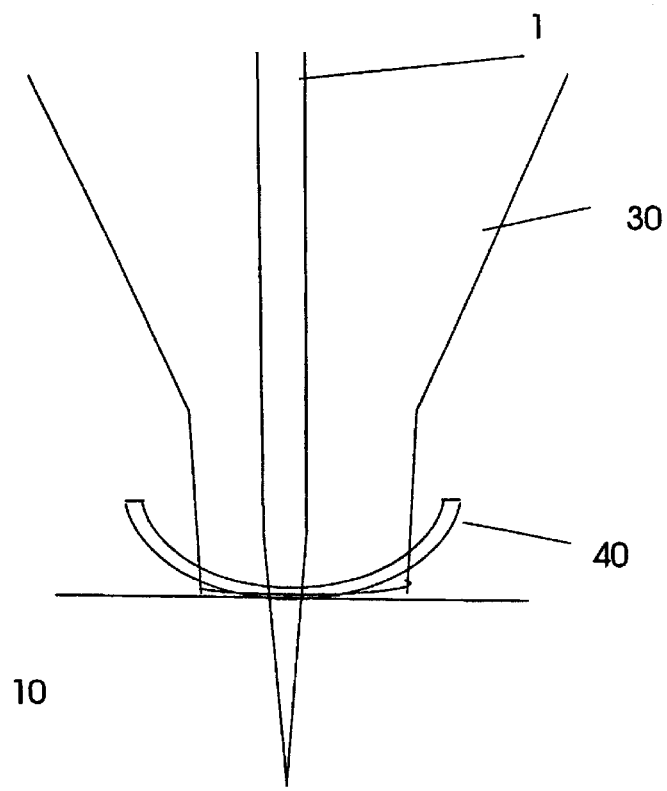

FIGS. 4A and 4B show a further example of the present invention. Referring to FIG. 4A, a needle 1, driven in the same manner as the earlier examples, is retained within a housing 30 which contains a substance 22 to be delivered into skin 10. A substance 22 is retained in the housing 30 by a septum 40 which, in use, engages with the surface of the skin. The septum 40 is preferably an elastomer, such as silicone rubber. As can be seen from FIG. 4B, in use, the needle 1 is driven through the septum 40 and into the skin 10. As with previous examples, withdrawal of the needle 1 creates a partial vacuum in the hole generated by the needle 1, drawing substance 22 into the skin 10. Because the septum 40 is an elastomer, withdrawal of the needle 1 back up into the housing 30 enables the septum 40 to close and seal in the substance 22, preventing contamination of the substance 22 by skin debris and the external atmosphere, as well as protecting a user from needle-stick injury.

Figure 5:
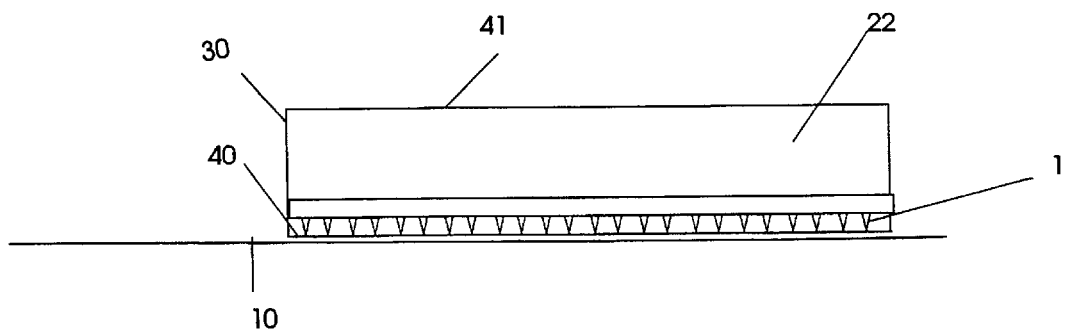

FIG. 5 shows a further example of the present invention which also employs a septum 40. In this example, an array of needles 1 is provided. It will be appreciated that, in the previous examples, an array of needles, rather than a single needle 1, could be employed using the same principles. In the example of FIG. 5, a housing 30 defines a substance retaining core in which substance 22 is held prior to delivery. The septum 40 may have an adhesive formed thereon so that the apparatus of this example can be attached to the skin 10 and activated at regular intervals. In this example, a user applies pressure to the upper surface 41 of the housing 30, urging one or more needles 1 to pass through the septum into the skin 10. As user force is removed, the needle or needles 1 pass back up through the septum 40, the septum 40 sealing itself after substance 22 has been drawn through into the skin 10.

Figure 6A:
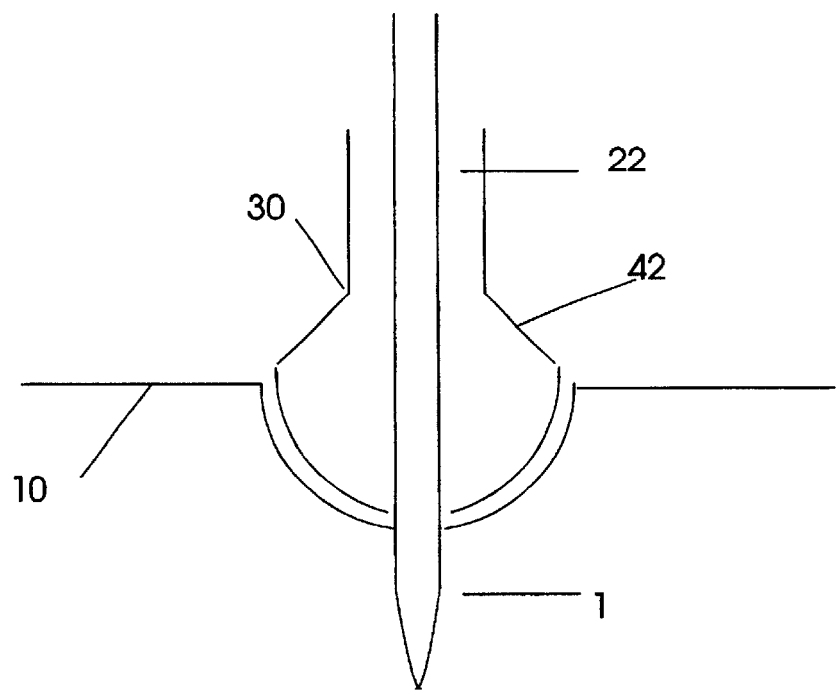
Figure 6B:
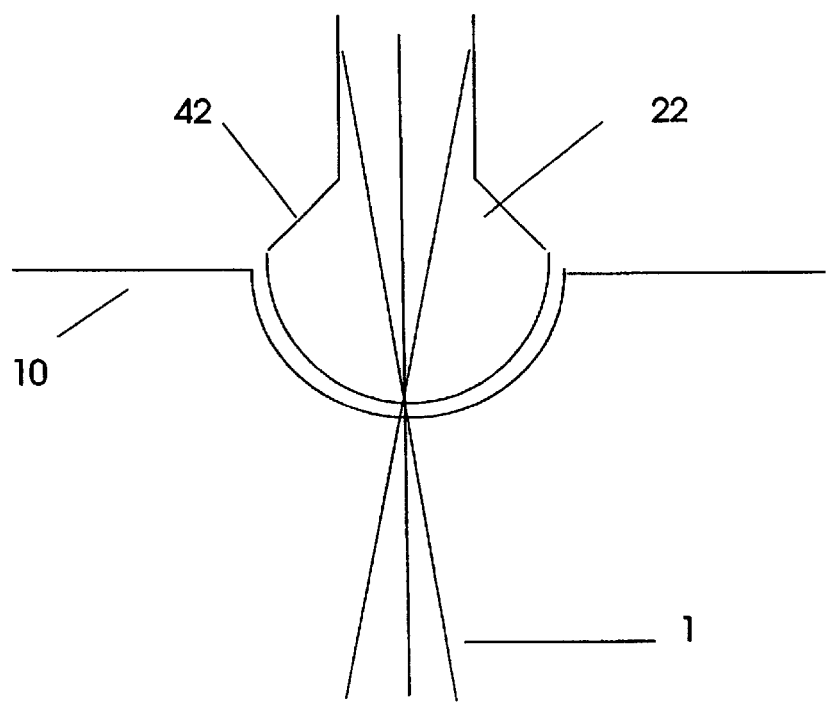

FIGS. 6A and 6B show further examples of the present invention in which the housing 30 has a convex skin engaging surface 42. The operation of examples of these figures is generally the same as previous examples, although the skin engaging surface 42 is arranged to stretch the skin prior to insertion of needle 1. This reduces the damage caused to the skin 10 by the needle 1, by controlling more precisely needle entry and reducing the possibility of lateral movement of the needle during deployment.

The arrangement of FIG. 6B has a skin engaging surface 42 which is arranged so that the angle of deployment of the needle 1 can be altered, either manually or mechanically by the apparatus. The ability to alter the angle of entry is useful to gain multiple holes through a single surface puncture to increase the local dose whilst minimising skin damage/infection risk when the apparatus is to be drawn across the surface of the skin, so that damage to the skin 10 is minimised.

Figure 7:
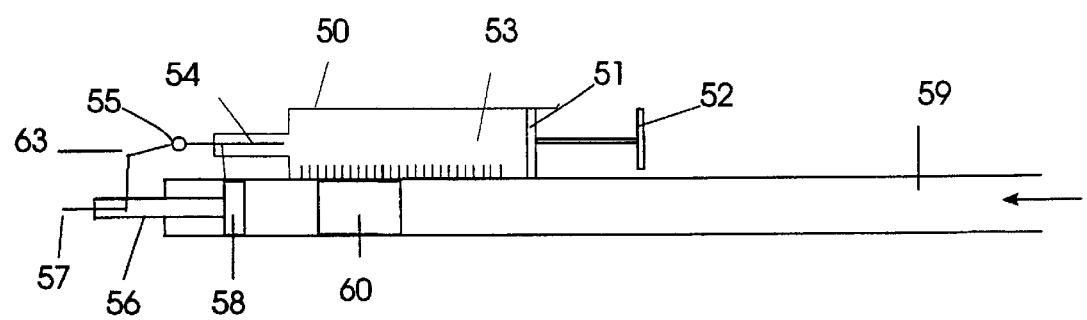
Figure 7A:
Figure 7B:

Referring to FIG. 7 a syringe 50 has a piston 51 mounted within it which can be depressed by handle 52. There is an outlet 54 from the syringe so that, when piston 51 is depressed, a substance in the body of the syringe 53 is forced out through the outlet 54. Attached to the outlet by a Luer connector 55 is one end of needle 63. The needle 63 is flexible and fixed to a holder 56 and mounted in a sliding flexible tube. The needle can b a zig-zag shape or coiled as shown in FIGS. 7a and 7b. Attached to holder 56 is a striker plate 58 which is the end piece of the needle 63 and which is slidably mounted within conduit 59, there is a block 60 positioned in the conduit. The end A of the conduit 59 is connected to pneumatic pump or the like so that air under pressure can enter the conduit and propel the block 60 down the conduit to strike plate 58. Reversal of the direction of the air in the conduit will cause the block 60 to be sucked back to the end of the conduit.

In use the substance to be injected is placed in the syringe 50 and the block 60 is at the end of conduit 59 remote from the needle 57. The needle 57 is placed against the surface to be injected and a pulse of high pressure air is sent down conduit 59 so to propel block 60 at the required high speed i.e. above 1 meter per sec, down conduit 59 to strike plate 58. The needle is then driven into the surface and, by having three blocks three impacts are made on the plate 58 and the needle penetrates in three steps. When the needle has penetrated the surface the piston 51 in the syringe 50 is depressed and the substance in the syringe is injected into the surface.

Figure 8:
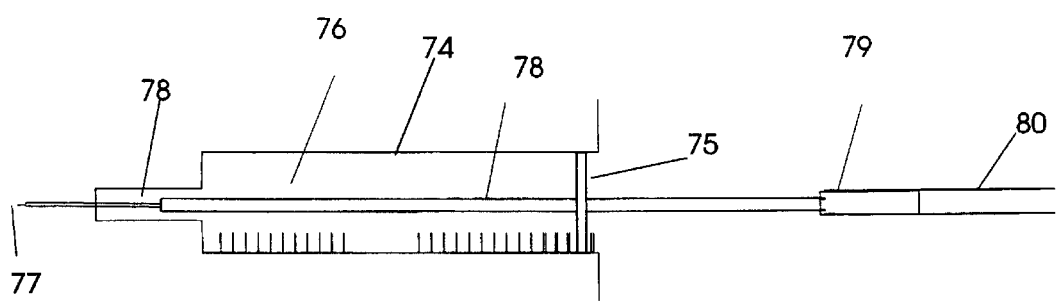
FIG. 8 is a view of a seventh example of the invention.

Referring to FIG. 8 a syringe 74 has a needle 77 attached to one end and the needle has openings at 73 whereby a substance in the syringe can enter the needle. An extension 78 to the needle 77 passes through the piston 75 and terminates in a striker plate 79. The striker plate is positioned in conduit 90 down which blocks can be propelled pneumatically to strike plate 79.

In use the syringe is filled with the substance to be injected and the needle 77 is placed against the surface, a block or blocks are propelled down conduit 80 in a similar way to that described for FIG. 7 and strike plate 79 and so drive the needle into the surface. When the needle has penetrated the surface to the required depth the piston 75 is depressed and the substance injected into the surface.

It will be appreciated that all of the embodiments of the present invention can be arranged to deliver many different substances into skin. The substance may be a traditional tattoo dye, a temporary dye, a drug, a gene therapy substance, a particulate substance, a vaccine, nutrients, carriers, diagnostic material, water, saline for example.

In all the examples of the present invention, there may be provided an end stop on the needle to prevent excessive entry of the needle into the skin for reasons of safety or depth control. This stop control enables the needle to be brought to a stop very rapidly and this aids the injection of the substance into the surface.

There may also be provided electrical or mechanical control of the depth of entry which is capable of adjustment by an operator. The control of depth of penetration may alternatively be automatic, and such arrangement might be provided by measuring a current passing through needle, the skin, and a conductive detecting element positioned oh the skin, the value of the current being proportional to the depth of entry of the needle 1. The applied voltage may be pulsed with a variety of waveforms in order to reduce perceived pain, when required.

What is claimed is:

1. Apparatus for injecting a substance into a surface, such as the skin of a human being, animal or other organic matter, the apparatus comprising:
   (a) at least one needle;
   (b) means for supplying the substance to the tip of the needle;
   (c) a driving means for driving the needle at a velocity in the range of 1 meter per second to 100 meters per second in which in use the majority of the energy for penetration comes from the momentum of the needle and associated moving parts and not from the continued force of the driving means.

2. Apparatus as claimed in claim 1 in which the driving means drives the needle at 5 to 50 meters per second.

3. Apparatus as claimed in claim 1 in which the driving means drives the needle at 6 to 35 meters per second.

4. Apparatus as claimed in claim 1 in which the driving means is pneumatically operated.

5. An apparatus as claimed in claim 1 in which there is a stopping means incorporated in the driving means adapted to bring the needle to a rapid stop at a predetermined depth of penetration.

6. An apparatus as claimed in claim 4 in which there is a stopping means incorporated in the driving means adapted to bring the needle to a rapid stop at a predetermined depth of penetration.

7. Apparatus as claimed in claim 1 in which there is a withdrawal means adapted to withdraw the needle from the surface.

8. Apparatus as claimed in claim 7 in which the driving means incorporates a means to drive the needle into the surface in a plurality of stages.

9. Apparatus as maimed in claim 1 in which the diameter of the one or more needles is in the range of 10 to 1000 microns and are arranged so that they form from 1 to 5000 holes per square centimeter.

10. An apparatus as claimed in claim 1 in which, in use the majority of the energy for penetration comes from the momentum of the needle and associated moving parts and not from the continued force of the driving means.

11. An apparatus as claimed in claim 5 in which, in use the majority of the energy for penetration comes from the momentum of the needle and associated moving parts and not from the continued force of the driving means.

12. Apparatus as claimed in claim 1 in which there is an end piece which forms part of, or is connected to the end of the needle which end piece is positioned at one end of a conduit, the said driving means comprising a block slidably mounted in the conduit and a pneumatic means adapted to apply a pneumatic force at one end of the conduit to propel the block down the conduit, so that the block strikes the said end piece.

13. Apparatus as claimed in claim 5 in which there is an end piece which forms part of, or is connected to the end of the needle which end piece is positioned at one end of a conduit, the said driving means comprising a block slidably mounted in the conduit and a pneumatic means adapted to apply a pneumatic force at one end of the conduit to propel the block down the conduit, so that the block strikes the said end piece.

14. Apparatus as claimed in claim 12 in which there are means to generate a pulse of air in the conduit which propels the block down the conduit.

15. Apparatus as claimed in claim 14 in which there are block withdrawal means to return the block to its original position by reduction of pressure in the conduit.

16. Apparatus as claimed in claim 13 in which the driving means applies a plurality of pulsed impulses to the block and the is a block withdrawal means to withdraw the block back down the conduit between pulses to its original position by reduction of pressure in the conduit.

17. Apparatus as claimed in claim 12 in which there are two or more blocks mounted within the conduit so that, in use, a plurality of blows impact on the end piece.

18. Apparatus as claimed in claim 1 in which the needle is separate and adjacent to a syringe containing the substance to be injected with one and of the needle fluidically and flexibly, connected to the end of the syringe and there being sufficient flexibility in this connection so that rapid acceleration and movement of the needle is not significantly inhibited by its connection to the syringe.

19. Apparatus as claimed in claim 12 in which the needle is separate and adjacent to a syringe containing the substance to be injected with one end of the needle fluidically and flexibly connected to the and of the syringe and there being sufficient flexibility in this connection so that rapid acceleration and movement of the needle is not significantly inhibited by its connection to the syringe.

20. Apparatus as claimed in claim 18 in which the needle is coiled, looped or zig-zagged.

21. Apparatus as claimed in claim 1 in which there is a syringe which has a piston mounted therein with the said needle projecting through the end of the syringe and the other end of the needle having an extension projecting through the piston so the end of the extension can be struck by the driving means to drive the needle into the surface, there being a connection means between and the needle and the syringe whereby a substance in the syringe passes through the needle from the syringe as the piston is depressed.

22. Apparatus as claimed in claim 12 in which there is a syringe which has a piston mounted therein with the said needle projecting through the end of the syringe and the other end of the needle having an extension projecting through the piston so the end of the extension can be struck by said block to drive the needle into the surface, there being a connection means between the needle and the syringe whereby a substance in the syringe passes through the needle from the syringe as the piston is depressed.

23. Apparatus as claimed in claim 1 in which part of the momentum of the said block is transferred to the syringe to induce pressure which injects a quantity of the substance to be injected into the skin.

24. Apparatus as claimed in claim 1 in which the mass of the needle and associated moving parts is from 0.01 to 2.5 grams.

25. Apparatus as claimed in claim 23 in which the mass of the needle and associated moving parts is from 0.01 to 2.5 grams.

26. Apparatus as claimed in claim 1 in which there is a needle guide through which the needle can slide in use to restrict transaxial or lateral movement of the needle.

27. An apparatus as claimed in claim 26 in which the needle guide restricts the transaxial or lateral movement of the needle to below +/−2 degrees.

28. Apparatus as claimed in claim 1 in which the needle is hollow with at least one aperture connecting to core directly adjacent to the tip to allow injections to be made at a depth of less than 1 mm below the skin surface.

29. An apparatus as claimed in claim 1 in which the needle has substantially non-cutting tip with substantially no sharpened edges or blades with smooth, tapered, radiused or beveled edges or surfaces.

30. Apparatus as claimed in claim 29 in which the needle is conical or with a radiused point and one or more slots are present which connect the core to the exterior to allow, in use, delivery of the substance below skin surface and in which when the needle is entering the skin the one or more slots are substantially closed to prevent entry of external material or tissue into the core.

31. Apparatus as claimed in claim 30 in which when fluidic pressure is applied from the care to the exterior the dimensions of the one or more slots increases to allow greater flow of fluidic substance.

32. Apparatus as claimed in claim 30 in which the one or more slots are linear and parallel to the needle axis, inclined at an angle to the axis, spiral in form or are arranged to define a moveable flap which closes like a valve when external pressure is applied to the needle and opens like a valve when internal pressure is applied.

33. An apparatus as claimed in claim 1 in which the needle has a blunt tip.

34. Apparatus as claimed in claim 12 in which there are means to generate is pulse of air in the conduit which propels the block down the conduit.

35. Apparatus as claimed in claim 14 in which there are block withdrawal means to return the block to its original position by redaction of pressure in the conduit.

36. Apparatus as claimed in claim 13 in which the driving means applies a plurality of pulsed impulses to the block and there is a block withdrawal means to withdraw the block back down the conduit between pulses to its original position by reduction of pressure in the conduit.

37. Apparatus as claimed in claim 12 in which there are two or more blocks mounted within the conduit so that, in use, a plurality of blows impact on the end piece.

38. Apparatus as claimed in claim 1 in which the needle is separate and adjacent to a syringe containing the substance to be injected with one end of the needle fluidically and flexibly connected to the end of the syringe and there being sufficient flexibility in this connection so that rapid acceleration and movement of the needle is not significantly inhibited by its connection to the syringe.

39. Apparatus as claimed in claim 12 in which the needle is separate and adjacent to a syringe containing the substance to be injected with one end of the needle fluidically and flexibly connected to the end of the syringe and there being sufficient flexibility in this connection so that rapid acceleration and movement of the needle is not significantly inhibited by its connection to the syringe.

40. Apparatus as claimed in claim 18 in which the needle is coiled, looped or zig-zagged.

41. Apparatus as claimed in claim 1 in which there is a syringe which has a piston mounted therein with the said needle projecting through the end of the syringe and the other end of the needle having an extension projecting through the piston so the end of the extension can be struck by the driving means to drive the needle into the surface, there being a connection means between and the needle and the syringe whereby a substance in the syringe passes through the needle from the syringe as the piston is depressed.

42. Apparatus as claimed in claim 12 in which there is a syringe which has a piston mounted therein with the said needle projecting through the end of the syringe and the other end of the needle having an extension projecting through the piston so the end of the extension can be struck by said block to drive the needle into the surface, there being a connection means between and the needle and the syringe whereby a substance in the syringe passes through the needle from the syringe as the piston is depressed.

43. Apparatus as claimed in claim 23 in which part of the momentum of the said block is transferred to the syringe to induce pressure which injects a quantity of the substance to be injected into the skin.

44. Apparatus as claimed in claim 1 in which the mass of the needle and associated moving parts is from 0.01 to 2.5 grams.

45. Apparatus as claimed in claim 1 in which the mass of the needles and associated moving parts is from 0.01 to 2.5 grams.

46. Apparatus as claimed in claim 1 in which there is a needle guide through which the needle can slide in use to restrict transaxial or lateral movement of the needle.

47. Apparatus as claimed in claim 26 in which the needle guide restricts the transaxial or lateral movement of the needle to below +/−2 degrees.

48. Apparatus as claimed in claim 1 in which the needle is hollow with at least one aperture connecting to core directly adjacent to the tip to allow injections to be made are a depth of less than 1 mm below the skin surface.

49. An apparatus as claimed in claim 1 in which the needle has substantially non-cutting tip with substantially no sharpened edges or blades with smooth, tapered, radiused or beveled edge or surfaces.

50. Apparatus as claimed in claim 30 in which the needle is conical or with a radiused point end and one or more slots are present which connect the core to the exterior to allow, in use, delivery of the substance below skin surface and in which when the needle is entering the skin the one or more slots are substantially closed to prevent entry of external material or tissue into the core.

51. Apparatus as claimed in claim 30 in which when fluidic pressure is applied from the core to the exterior the dimensions of the one or more slots increases to allow greater flow of fluidic substance.

52. Apparatus as claimed in claim 30 in which the one or more slots are linear and parallel to the needle axis, inclined at an angle to the axis, spiral in form or are arranged to define a moveable flap which closes like a valve when external pressure is applied to the needle and opens like a valve when internal pressure is applied.

53. Apparatus for injecting a substance into a surface, such as the skin of a human being, animal or other organ matter, the apparatus comprising:
(d) at least one needle;
(e) means for supplying the substance to the tip of the needle a driving means for driving the needle at a velocity in the range of 5 meters per second to 100 meters per second in which the driving means is adapted to deliver an impact to the needle to drive the needle.

54. An apparatus as claimed in claim 53 in which the driving means is adapted to accelerate the needle to an acceleration between 1 to 20,000 g.

55. An apparatus as claimed in claim 53 in which the needle has a blunt tip.

56. Apparatus as claimed in claim 53 in which the driving means drives the needle at 5 to 50 meters per second.

57. Apparatus as claimed in claim 53 in which the driving means drives the needle at 6 to 35 meters per second.

58. Apparatus as claimed in claim 54 in which the driving means is pneumatically operated.

59. An apparatus as claimed in claim 55 in which there is stopping means incorporated in the driving means adapted to bring the needle to a rapid stop at a predetermined depth of penetration.

60. An apparatus as claimed in claim 53 in which there is stopping means incorporated in the driving means adapted to bring the needle to a rapid stop at a predetermined depth of penetration.

61. Apparatus as claimed as claim 53 in which there is a withdrawal means adapted to withdraw the needle from the surface.

62. Apparatus as claimed in claim 53 in which the driving means incorporates a means to drive the needle into the surface in a plurality of stages.

63. Apparatus as claimed in claim 53 in which the diameter of the one or more needles is in the range of 10 to 1000 microns and are arranged so that they form from 1 to 5000 holes per square centimeter.

64. An apparatus as claimed in claim 53 in which, in use the majority of the energy for penetration comes from the momentum of the needle and associated moving parts and not from the continued force of the driving means.

65. Apparatus as claimed in claim 53 in which there is an end piece which forms part of, or is connected to the end of the needle which end piece is positioned at one end of a conduit, the said driving means comprising a block slidably mounted in the conduit and a pneumatic means adapted to apply a pneumatic force at one end of the conduit to propel the block down the conduit, so that the block strikes the said end piece.

66. Apparatus as claimed in claim 53 in which there are means to generate a pulse of air in the conduit which propels the block down the conduit.

67. Apparatus as claimed in claim 53 in which there are one or more slots extending linear and parallel to the needle axis, inclined at an angle to the axis, spiral in form or are arranged to define a moveable flap which closes like a valve when external pressure is applied to the needle and opens like a valve when internal pressure is applied.

68. A method for injecting a substance into a surface which method comprises using an injector which consists of at least one needle and a means for supplying the substance to the tip of the needle in which method the needle is placed against the surface and the end of the needle struck by an impact to drive the needle into the surface at a velocity in the range of 1 to 100 meters per second and the substance supplied to the tip of the needle to inject the substance into the surface.

* * * * *